United States Patent [19]

Dickore et al.

[11] 4,240,820

[45] Dec. 23, 1980

[54] METHOD OF REGULATING THE GROWTH OF PLANTS

[75] Inventors: Karlfried Dickoré, Leverkusen; Klaus Lürssen, Bergisch-Gladbach, both of Fed. Rep. of Germany

[73] Assignee: Bayer Aktiengesellschaft, Leverkusen, Fed. Rep. of Germany

[21] Appl. No.: 29,969

[22] Filed: Apr. 13, 1979

[30] Foreign Application Priority Data

Apr. 21, 1978 [DE] Fed. Rep. of Germany ....... 2817449

[51] Int. Cl.³ ..................... A01N 43/08; A01N 43/10
[52] U.S. Cl. ............................................ 71/76; 71/73; 71/75; 260/347.3; 260/347.4; 260/347.5; 549/68; 549/69
[58] Field of Search .................. 71/76, 88, 90, 99, 73, 71/75

[56] References Cited

U.S. PATENT DOCUMENTS

| | | | |
|---|---|---|---|
| 3,352,663 | 11/1967 | Freund et al. ......................... | 71/88 |
| 3,536,473 | 10/1970 | Popoff et al. .......................... | 71/90 |
| 3,778,512 | 12/1973 | Krenzer et al. ..................... | 71/88 X |
| 3,828,001 | 8/1974 | Broad et al. ......................... | 71/90 X |
| 3,892,775 | 7/1975 | Kobinza ............................... | 71/90 X |
| 3,956,315 | 5/1976 | Kobinza ............................... | 71/90 X |

FOREIGN PATENT DOCUMENTS

2510936 10/1975 Fed. Rep. of Germany .

OTHER PUBLICATIONS

Gewald et al., Berichte, 99, 94–100, (1966).
Gewald, Berichte, 99, 1,002–1,007, (1966).
Gewald et al., Berichte, 99, 2,712–2,715, (1966).
Sauter et al., Arch. Pharm., 309, 914–919, (1976).

*Primary Examiner*—Donald G. Daus
*Assistant Examiner*—Diana G. Rivers
*Attorney, Agent, or Firm*—Sprung, Felfe, Horn, Lynch & Kramer

[57] ABSTRACT

Novel method for regulating the growth of plants which method comprises applying to the plants or their habitat, effective amounts of heterocyclic compound of the formula $$\begin{array}{c} R^1 \quad\quad R^4 \\ \phantom{xx} \\ R^2 \quad X \quad NH-R^3 \end{array} \quad (I)$$

in which
$R^1$ is alkyl or optionally substituted aryl,
$R^2$ is hydrogen, alkyl or optionally substituted aryl,
$R^3$ is hydrogen or the radical $$-\underset{\underset{Y}{\|}}{C}-R^5,$$

in which
Y is oxygen or sulfur and
$R^5$ is alkyl, haloalkyl, alkoxyalkyl, aryloxyalkyl, which is optionally substituted in the aryloxy part, alkoxy, optionally substituted aryl, optionally substituted aryloxy, monoalkylamino, dialkylamino, alkenylamino, dialkenylamino, optionally substituted arylamino, a 5-membered to 7-membered heterocyclic ring, bonded via nitrogen, or the radical $$-NH-N\underset{R^7}{\overset{R^6}{\diagup}}$$

in which
$R^6$ is hydrogen or alkyl and
$R^7$ is hydrogen or alkyl, or
$R^6$ and $R^7$, together with the adjacent nitrogen atom, are a 5-membered to 7-membered heterocyclic ring,
$R^4$ is cyano or the grouping $-COR^8$
in which
$R^8$ is alkoxy or amino, and X is oxygen or sulfur.

28 Claims, No Drawings

METHOD OF REGULATING THE GROWTH OF PLANTS

The present invention relates to methods of regulating the growth of plants, utilizing certain heterocyclic compounds.

It is known that certain thienylureas have herbicidal activity (see DT-OS (German Published Specification) No. 2,510,936). Furthermore, the synthesis of several 2-aminothiophenes and 2-aminofuranes has been described in the literature [see Ber. 99, 1,002–1,007 (1966), Ber. 99, 94–100 (1966) and Ber. 99, 2,712–2,715 (1966)]. It is also known that certain acyl-thiophenes can be used as starting materials for the preparation of pharmacolocically active compounds [see Arch. Pharm. 309, 914–919 (1976)].

It is also known that (2-chloroethyl)-trimethylammonium chloride has plant growth regulating properties (see U.S. Pat. No. 3,156,554). However, the activity of this substance is not always completely satisfactory, above all when low amounts are used.

It is likewise already known that certain 2-halogenoethane-sulphinic acids, for example 2-chloroethanesulphinic acid, and their derivatives can be used as plant growth regulators (see German Offenlegungsschrift (German Published Specification) No. 2,110,773). However, their action is also not always completely satisfactory, above all when low amounts are used.

In addition, it is known that certain 2-aminotetramethylene-thiophene derivatives, for example 2-acetamino-3-carbethoxy-4,5-tetramethylene-thiophene and 2-isopropylcarbonyl-amino-3-carbethoxy-4,5-tetramethylenethiophene, are suitable as plant growth regulators (see DT-OS (German Published Specification) No. 2,627,935). Nevertheless, the action of these substances is likewise not always adequate.

It has now been found that the heterocyclic compounds of the general formula

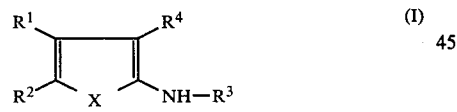 (I)

in which

R¹ represents alkyl or optionally substituted aryl,

R² represents hydrogen, alkyl or optionally substituted aryl,

R³ represents hydrogen or the grouping

in which

Y represents oxygen or sulphur and

R⁵ represents alkyl, halogenoalkyl, alkoxyalkyl, aryloxyalkyl, which is optionally substituted in the aryloxy part, alkoxy, optionally substituted aryl, optionally substituted aryloxy, monoalkylamino, dialkylamino, alkenylamino, dialkenylamino, optionally substituted arylamino, a 5-membered to 7-membered heterocyclic ring, bonded via nitrogen, or the grouping

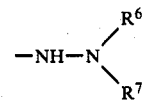

in which

R⁶ represents hydrogen or alkyl and

R⁷ represents hydrogen or alkyl, or

R⁶ and R⁷, together with the adjacent nitrogen atom, represent a 5-membered to 7-membered heterocyclic ring, R⁴ represents cyano or the grouping —COR⁸ in which R⁸ represents alkoxy or amino, and X represents oxygen or sulphur, have powerful plant growth regulating properties.

Accordingly, the present invention provides a method of regulating the growth of plants which comprises applying to the plants, or to a habitat thereof, a compound of the formula (I) alone or in admixture with a diluent or carrier.

Preferably, in formula (I), R¹ represents straight-chain or branched alkyl with 1 to 6 carbon atoms or aryl with 6 or 10 carbon atoms (phenyl and naphthyl being mentioned as examples) which optionally carries one or more substituents selected independently from halogen, alkyl with 1 to 4 carbon atoms, halogenoalkyl with 1 to 4 carbon atoms and 1 to 5 halogen atoms (especially fluorine atoms or chlorine atoms), alkoxy with 1 to 4 carbon atoms, alkylthio with 1 to 4 carbon atoms, alkylsulphonyl with 1 to 4 carbon atoms and nitro, R² represents hydrogen, straight-chain or branched alkyl with 1 to 6 carbon atoms or aryl with 6 or 10 carbon atoms (phenyl and naphthyl being mentioned as examples) which optionally carries one or more substituents selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms, alkylsulphonyl with 1 to 4 carbon atoms and nitro, R³ represents hydrogen or the grouping

in which

Y represents oxygen or sulphur and

R⁵ represents straight-chain or branched alkyl with 1 to 6 carbon atoms; straight-chain or branched halogenoalkyl with 1 to 4 carbon atoms and 1 to 5 halogen atoms (especially fluorine or chlorine atoms); alkoxyalkyl with 1 to 4 carbon atoms in the alkyl part and 1 to 4 carbon atoms in the alkoxy part; aryloxyalkyl which has 6 or 10 carbon atoms in the aryloxy part and 1 to 4 carbon atoms in the alkyl part and optionally carries one or more substituents on the aryloxy part selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms, alkylsulphonyl with 1 to 4 carbon atoms and nitro; straight-chain or branched alkoxy with 1 to 4 carbon atoms; aryl with 6 or 10 carbon atoms (phenyl and naphthyl being mentioned as examples) which optionally carries one or more substituents selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms, alkylsulphonyl with 1 to 4 carbon atoms and nitro; aryloxy with 6 or 10 carbon atoms (phenoxy and naphthoxy being mentioned as examples) which optionally carries one or more substituents selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms, alkylsulphonyl with 1 to 4 carbon atoms and nitro; monoalkylamino with b 1 to 4 carbon atoms; dialkylamino with 1 to 4 carbon atoms in each alkyl group; alkenylamino with up to 4 carbon atoms; dialkenylamino with up to 4 carbon atoms in each alkenyl group; arylamino with 6 or 10 carbon atoms, which optionally carries one or more substituents selected independently from halogen, alkyl with 1 to 4 carbon atoms, halogenoalkyl with 1 to 4 carbon atoms and 1 to 5 halogen atoms (especially fluorine or chlorine atoms), alkoxy with 1 to 4 carbon atoms, alkylthio with 1 to 4 carbon atoms, alkylsulphonyl with 1 to 4 carbon atoms and nitro; a 5-membered to 7-membered saturated heterocyclic ring which is bonded via nitrogen and in which each of 1 to 3 carbon atoms can be replaced by oxygen, sulphur, —SO$_2$—, —NH— or —N(CH$_3$)— (examples of heterocyclic radicals of this type which may be mentioned being morpholinyl, thiomorpholinyl, pyrrolidinyl, piperidinyl, piperazinyl and hexahydroazepinyl); or the grouping

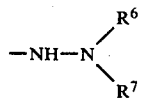

in which

R$^6$ represents hydrogen or alkyl with 1 to 4 carbon atoms and

R$^7$ represents hydrogen or alkyl with 1 to 4 carbon atoms, or

R$^6$ and R$^7$, together with the adjacent nitrogen atom, represent a 5-membered to 7-membered saturated heterocyclic ring in which each of 1 to 3 carbon atoms can be replaced by oxygen, sulphur, —SO$_2$—, —NH— or —N(CH$_3$)— (examples of heterocyclic radicals of this type which may be mentioned being morpholinyl, thiomorpholinyl, pyrrolidinyl, piperidinyl, piperazinyl and hexahydroazepinyl), and R$^4$ represents cyano or the grouping —COR$^8$, in which R$^8$ represents alkoxy with 1 to 4 carbon atoms or amino.

Surprisingly, the heterocyclic compounds of the formula (I) which can be used according to the invention exhibit a better plant growth regulating activity than (2-chloroethyl)-trimethylammonium chloride, which is known from the state of the art, and 2-chloroethane-sulphinic acid, which is likewise known, these substances being recognized as substances of good activity with the same type of action. The heterocyclic compounds of the formula (I) also possess a more powerful activity than 2-acetamido-3-carbethoxy-4,5-tetramethylene-thiophene and 2-isopropyl-carbonyl-amino-3-carbethoxy-4,5-tetramethylene-thiophene, which are the substances already known and of the same type of action which are most similar chemically. The substances which can be used according to the invention thus represent a valuable enrichment of the art.

Compounds of the formula (I) which can particularly preferably be used are those in which R$^1$ represents methyl, ethyl, n-propyl, isopropyl, n-butyl, sec.-butyl or tert.-butyl, or phenyl or naphthyl, either of which is optionally substituted by fluorine, chlorine, bromine, methyl, ethyl, n-propyl, isopropyl, trifluoromethyl, trichloromethyl, methoxy, ethoxy, methylthio, ethylthio, methylsulphonyl, ethylsulphonyl and/or nitro, R$^2$ represents hydrogen, methyl, ethyl, n-propyl, isopropyl, n-butyl, sec.-butyl or tert.-butyl, or phenyl or naphthyl, either of which is optionally substituted by fluorine, chlorine, bromine, methyl, ethyl, n-propyl, isopropyl, trifluoromethyl, trichloromethyl, methoxy, ethoxy, methylthio, ethylthio, methylsulphonyl, ethylsulphonyl and/or nitro, R$^3$ represents hydrogen or the grouping

in which Y represents oxygen or sulphur and R$^5$ represents methyl, ethyl, n-propyl, isopropyl, n-butyl, sec.-butyl, tert.-butyl, chloromethyl, dichloromethyl, trichloromethyl, chloroethyl, dichloroethyl, trifluoromethyl, methoxymethyl, ethoxymethyl, methoxyethyl, ethoxyethyl or phenoxyalkyl which has 1 or 2 carbon atoms in the alkyl part and is optionally substituted in the phenoxy part by fluorine, chlorine, bromine, methyl, ethyl, trifluoromethyl, trichloromethyl, methoxy, ethoxy, methylthio, ethylthio, methylsulphonyl, ethylsulphonyl and/or nitro, or R$^5$ represents methoxy, ethoxy, n-propoxy, isopropoxy, n-butoxy, sec.-butoxy or tert.-butoxy, or phenyl or naphthyl, either of which is optionally substituted by fluorine, chlorine, bromine, methyl, ethyl, n-propyl, isopropyl, n-butyl, sec.-butyl, tert.-butyl, trifluoromethyl, trichloromethyl, methoxy, ethoxy, methylthio, ethylthio, methylsulphonyl, ethylsulphonyl and/or nitro, or R$^5$ represents phenoxy or naphthoxy, either of which is optionally substituted by fluorine, chlorine, bromine, methyl, ethyl, n-propyl, isopropyl, n-butyl, sec.-butyl, tert.-butyl, trifluoromethyl, trichloromethyl, methoxy, ethoxy, methylthio, ethylthio, methylsulphonyl, ethylsulphonyl and/or nitro, or R$^5$ represents methylamino, ethylamino, n-propylamino, isopropylamino, n-butylamino, dimethylamino, diethylamino, di-n-propylamino, allylamino, diallylamino or phenylamino which is optionally substituted by fluorine, chlorine, bromine, methyl, ethyl, n-propyl, isopropyl, n-butyl, sec.-butyl, tert.-butyl, trifluoromethyl, trichloromethyl, methoxy, ethoxy, methylthio, ethylthio, methylsulphonyl, ethylsulphonyl and/or nitro, or R$^5$ represents one of the heterocyclic radicals morpholinyl, thiomorpholinyl, pyrrolidinyl, piperidinyl, piperazinyl and hexahydroazepinyl, in each case bonded via nitrogen, or R$^5$ represents the grouping

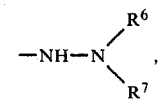

in which $R^6$ represents hydrogen, methyl or ethyl and $R^7$ represents hydrogen, methyl or ethyl, or $R^6$ and $R^7$, together with the adjacent nitrogen atom, represent morpholinyl, thiomorpholinyl, pyrrolidinyl, piperidinyl, piperazinyl or hexahydroazepinyl, and $R^4$ represents cyano or the grouping -$COR^8$, in which $R^8$ represents methoxy, ethoxy, n-propoxy, isopropoxy, n-butoxy or amino.

Specific examples which may be mentioned of compounds of the formula (I), in addition to the substances listed in the preparative examples, are: 2-amino-3-methoxycarbonyl-4-methyl-5-phenyl-thiophene, 2-amino-3-n-propoxycarbonyl-4-methyl-5-phenyl-thiophene, 2-amino-3-n-butoxycarbonyl-4-methyl-5-phenyl-thiophene, 2-amino-3-methoxycarbonyl-4-methyl-5-phenyl-furane, 2-amino-3-n-propoxycarbonyl-4-methyl-5-phenyl-furane, 2-amino-3-n-butoxycarbonyl-4-methyl-5-phenyl-furane, 2-amino-3-cyano-4-methylthiophene, 2-amino-3-cyano-4-methyl-furane, 2-phenylcarbonyl-amino-3-ethoxycarbonyl-4,5-dimethyl-thiophene, 2-(4-chlorophenylcarbonyl)-amino-3-ethoxycarbonyl-4,5-dimethylthiophene, 2-(4-methylphenylcarbonyl)-amino-3-ethoxycarbonyl-4,5-dimethyl-thiophene, 1-(3-cyano-4-isopropyl-5-methylthien-2-yl)-3-methyl-urea, 1-(3-cyano-4-tert.-butyl-5-methyl-thien-2-yl)-3,3-dimethyl-urea, 2-amino-3-aminocarbonyl-4,5-dimethyl-thiophene, 2-acetylamino-3-aminocarbonyl-4,5-dimethyl-thiophene, 2-isobutyrylamino-3-aminocarbonyl-4,5-dimethyl-thiophene and 4-tert.-butyl-3-cyano-2-ethoxyacetylamino-5-methyl-furane.

Some of the heterocyclic compounds of the formula (I) which can be used according to the invention are known [see DT-OS (German Published Specification) No. 2,510,936, Ber. 99, 94–100 (1966), Ber. 99, 1,002–1,007 (1966), Ber. 99, 2,712–2,715 (1966) and Arch. Pharm. 309, 914–919 (1976)].

Certain examples of the active compounds which can be used according to the invention have not been described hitherto in the literature, but they can be prepared in a simple manner by processes which are known in principle. Thus, heterocyclic compounds of the formula (I) are obtained when (a) keto compounds of the general formula $$R^1-C=O$$
$$R^2-CH_2$$
(II), in which
$R^1$ and $R^2$ have the meanings stated above, are reacted with cyano compounds of the general formula

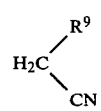
(III), in which
$R^9$ represents cyano or the radical -$COR^{10}$, in which
$R^{10}$ represents alkyl, and with sulphur in the presence of an inert organic solvent, such as ethanol or dimethylformamide, and in the presence of a base, such as triethylamine or morpholine, at temperatures between 20° and 80° C., or when (b) ethylenes of the general formula

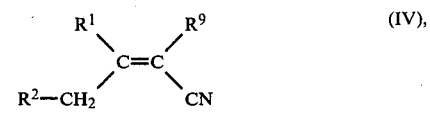
(IV), in which
$R^1$, $R^2$ and $R^9$ have the meanings stated above, are reacted with sulphur in the presence of an inert organic solvent, such as ethanol or dimethylformamide, and in the presence of a base, such as triethylamine or morpholine, at temperatures between 20° C. and 80° C., or when (c) keto compounds of the general formula $$R^1-C=O$$
$$R^2-CH-OH$$
(V), in which
$R^1$ and $R^2$ have the meanings stated above, are reacted with cyano compounds of the formula (III) in the presence of an inert organic solvent, such as ethanol or dimethylformamide, and in the presence of a base, such as triethylamine or morpholine, at temperatures between 20° C. and 50° C., or when (d) compounds which can be prepared according to process variants (a), (b) and (c), of the general formula

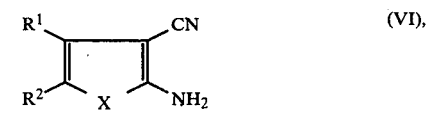
(VI), in which
$R^1$, $R^2$ and X have the meanings stated above, are converted into the corresponding 3-aminocarbonyl derivatives with strong acids, such as sulphuric acid, if appropriate in the presence of an inert diluent and at temperatures between 80° C. and 120° C., or when (e) compounds which can be prepared according to process variants (a)-(d), of the general formula

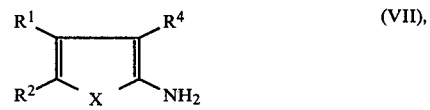
(VII), in which
$R^1$, $R^2$, $R^4$ and X have the meanings stated above, are reacted with halogen compounds of the formula $$Hal-C-R^5$$
$$\parallel$$
$$Y$$
(VIII), in which
$R^5$ and Y have the meanings stated above and Hal represents chlorine or bromine, in the presence of an inert organic solvent, such as toluene or dimethylformamide, and if appropriate in the presence of an acid-binding agent, such as pyridine or triethylamine, and at temperatures between 0° C. and 120° C., preferably between 20° C. and 100° C., or when (f) compounds which can be prepared according to process variants (a)-(d), of the general formula

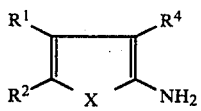 (VII), in which

R$^1$, R$^2$, R$^4$ and X have the meanings stated above, are reacted with anhydrides of the general formula (R$^{11}$—CO)$_2$O  (IX), in which R$^{11}$ represents alkyl, halogenoalkyl, alkenyl or optionally substituted aryl, if appropriate in the presence of an organic solvent, such as, for example, the acid on which the anhydride is based, and at temperatures between 20° C. and 150° C., preferably between 60° C. and 100° C., or when (g) compounds which can be prepared according to process variants (a)-(d), of the general formula

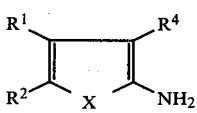 (VII), in which

R$^1$, R$^2$, R$^4$ and X have the meanings stated above, are reacted with isocyanates or isothiocyanates of the general formula

R$^{11}$—NCY  (X), in which

R$^{11}$ and Y have the meanings stated above, in the presence of an inert organic solvent, such as toluene, at temperatures between 0° C. and 120° C., preferably between 20° C. and 50° C., or when (h) compounds which can be prepared according to process variants (a)-(d), of the general formula

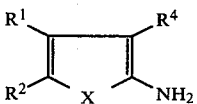 (VII), in which

R$^1$, R$^2$, R$^4$ and X have the meanings stated above, are reacted with phosgene or thiophosgene in the presence of an inert organic solvent, such as ethylene chloride, at temperatures between 40° C. and 120° C., preferably between 60° C. and 100° C., and the isocyanates or isothiocyanates thereby formed, of the general formula

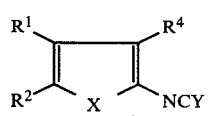 (XI), in which R$^1$, R$^2$, R$^4$, X and Y have the meanings stated above, are reacted with compounds of the general formula

H—R$^{12}$  (XII), in which

R$^{12}$ represents alkoxy, aryloxyalkoxy which is optionally substituted in the aryloxy part, optionally substituted aryloxy, monoalkylamino, dialkylamino, alkenylamino, dialkenylamino, optionally substituted arylamino, a 5-membered to 7-membered heterocyclic ring, which is bonded via nitrogen, or the grouping

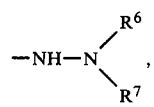

in which R$^6$ and R$^7$ have the meanings stated above, if appropriate in the presence of an inert organic solvent, such as toluene, at temperatures between 0° C. and 120° C., preferably 20° C. and 50° C.

The compounds of the formulae (II), (III), (IV), (V), (VIII), (IX), (X) and (XII) required as starting materials or reactants are known or can be prepared by processes which are known in principle.

Further details of the synthesis of the heterocyclic compounds which can be used according to the invention can be found in the preparative examples.

The active compounds which can be used according to the invention engage in the metabolism of the plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, while vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants as harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and ULV-formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other known active compounds, such as fungicides, insecticides, acaricides and herbicides, and also as a mixture with fertilizers and with other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomizing, scattering, dusting, foaming and gassing. Furthermore it is possible to apply the active compounds in accordance with the ultra-low-volume method, to spread the active compound preparation or the active compound itself on plants or parts of plants or to inject the active compound preparation or the active compound itself into the soil. It is also possible to treat the seeds of plants.

The active compound concentrations can be varied within a substantial range. In general, 0.01 to 50 kg, preferably 0.05 to 10 kg, of active compound are used per hectare of soil surface.

The examples which follow show the activity of the compounds according to the invention as growth regulators without excluding the possibility of further applications as growth regulators.

In these Examples, the compounds according to the present invention are each identified by the number (given in brackets) of the corresponding preparative Example, which will be found later in this specification. The known comparison compounds are identified as follows:

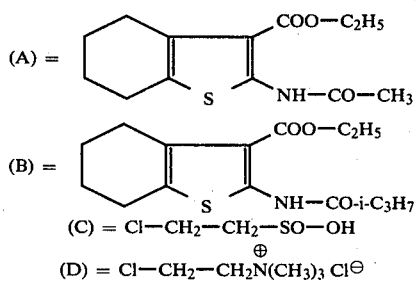

(C) = Cl—CH$_2$—CH$_2$—SO—OH (D) = Cl—CH$_2$—CH$_2$N(CH$_3$)$_3$ $\oplus$ Cl$^\ominus$

EXAMPLE A

Inhibition of growth of grass (*Festuca pratensis*)

Solvent: 30 parts by weight of dimethylformamide.

Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Grass (*Festuca pratensis*) was grown in plastic pots of size 7 cm×7 cm and when it had grown to a height of about 5 cm was sprayed with the preparation of active compound until dripping wet. After 3 weeks, the additional growth was measured and the inhibition of growth in percent of the additional growth of the untreated control plants was calculated. 100% meant that growth had stopped and 0% denoted a growth corresponding to that of the control plants.

The active compounds, concentrations and results can be seen from the table which follows:

Table A

| Active compound | Inhibition of growth of grass (*Festuca pratensis*) | |
|---|---|---|
| | Active compound concentration in % | Inhibition of growth in % |
| — (control) | — | — |
| (A) | 0.05 | 0 |
| (B) | 0.05 | 5 |
| (72) | 0.05 | 40 |
| (54) | 0.05 | 25 |
| (61) | 0.05 | 30 |
| (30) | 0.05 | 45 |
| (34) | 0.05 | 100 |
| (23) | 0.05 | 45 |

EXAMPLE B

Acceleration of ripening of tomatoes

Solvent: 30 parts by weight of dimethylformamide

Emulsifier: 1 part by weight of polyoxyethylene sorbitan monolaurate

To produce a suitable preparation of active compound, 1 part by weight of active compound was mixed with the stated amounts of solvent and emulsifier and the mixture was made up to the desired concentration with water.

Tomato plants were grown out of doors in the usual manner, until about half the fruits were red-colored. In this stage, the plants were sprayed with the preparations of active compound until dripping wet. After 2 weeks, the coloring of the fruits was rated and was designated on a scale of 0 to 3 as follows:

0 = no acceleration of ripening (like the untreated control)
1 = slight acceleration of ripening
2 = moderate acceleration of ripening
3 = strong acceleration of ripening The active compounds, active compound concentrations and results can be seen from the table which follows.

Table B

| Active compound | Acceleration of ripening of tomatoes | |
|---|---|---|
| | Active compound concentraton in % | Acceleration of ripening |
| — (control) | — | 0 |
| (C) | 0.2 | 1 |

Table B-continued

| Acceleration of ripening of tomatoes | | |
|---|---|---|
| Active compound | Active compound concentraton in % | Acceleration of ripening |
| (1) | 0.2 | 2 |

EXAMPLE C

Inhibition of growth of barley

Solvent: 30 parts by weight of dimethylformamide.

Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Barley plants were grown to the 2-leaf stage in a greenhouse. In this stage, the plants were sprayed with the preparations of active compound until dripping wet. After 3 weeks, the additional growth was measured on all plants and the inhibition of growth in % of the additional growth of the control plants was calculated. 100% meant that growth had stopped and 0% denoted a growth corresponding to that of the control plants.

The active compounds, active compound concentrations and results can be seen from the table which follows:

Table C

| Inhibition of growth of barley | | |
|---|---|---|
| Active compound | Active compound concentration in % | Inhibition of growth in % |
| — (control) | — | 0 |
| (D) | 0.05 | 40 |
| (A) | 0.05 | 15 |
| (B) | 0.05 | 5 |
| (72) | 0.05 | 95 |
| (57) | 0.05 | 55 |
| (55) | 0.05 | 50 |
| (67) | 0.05 | 60 |

EXAMPLE D

Inhibition of growth of wheat

Solvent: 30 parts by weight of dimethylformamide.

Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Wheat plants were grown to the 2-leaf stage in a greenhouse. In this stage, the plants were sprayed with the preparations of active compound until dripping wet. After 3 weeks, the additional growth was measured on all plants and the inhibition of growth in % of the additional growth of the control plants was calculated. 100% meant that growth had stopped and 0% denoted a growth corresponding to that of the control plants.

The active compounds, active compound concentrations and results can be seen from the table which follows.

TABLE D

| Inhibition of growth of wheat | | |
|---|---|---|
| Active compound | Active compound concentration in % | Inhibition of growth in % |
| — (control) | — | 0 |
| (D) | 0.05 | 45 |
| (A) | 0.05 | 5 |
| (B) | 0.05 | 0 |
| (72) | 0.05 | 85 |

EXAMPLE E

Stimulation of ethylene biosynthesis

Solvent: 30 parts by weight of dimethylformamide.

Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Pieces of leaf of identical size were punched from soya bean leaves. A constant number of pieces of leaf was incubated for 1 hour in Petri dishes which were filled with 10 ml of the active compound preparations or with corresponding control solutions without active compounds. Thereafter, the pieces of leaf were introduced into vessels which were closed air-tight. A part of the active compound preparations was also introduced into these vessels. After 24 hours the ethylene which had collected in the vessels was determined by customary methods of detection. The evolution of ethylene from the pieces of leaf treated with the preparations of active compound was compared with the evolution of ethylene of the controls.

The plant hormone ethylene affects numerous processes during the development of the plants. An increase in ethylene biosynthesis, such as can be achieved with the substances according to the invention, makes it possible to control these processes. The following may be mentioned here as examples in which there is, in particular, commercial interest: detachment of fruit, acceleration of ripening of fruit and leaves, induction of flowering, germination of seeds, thinning-out of fruit, stimulation of latex flux, for example in hevea, and inhibition of growth, for example also to prevent the lodging of cereals.

The active compounds and the results can be seen from the table which follows.

Table E

| Stimulation of ethylene biosynthesis | |
|---|---|
| Active compound | Action |
| — (control) | no activity |
| (A) | no activity |
| (B) | no activity |
| (2) | activity |
| (1) | activity |
| (27) | activity |
| (38) | activity |
| (36) | activity |
| (39) | activity |
| (43) | activity |
| (62) | activity |
| (55) | activity |
| (67) | activity |
| (54) | activity |

Table E-continued

| Stimulation of ethylene biosynthesis | |
| --- | --- |
| Active compound | Action |
| (61) | activity |
| (70) | activity |

EXAMPLE F

Inhibition of growth of cotton

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 3 weeks, the additional growth was measured on all the plants and the inhibition of growth in % of the additional growth of the control plants was calculated. 100% meant that growth had stopped and 0% denoted a growth corresponding to that of the control plants.

The active compounds, active compound concentrations and results can be seen from the table which follows.

Table F

| Inhibition of growth of cotton | | |
| --- | --- | --- |
| Active compound | Active compound concentration in % | Inhibition of growth in % |
| — (control) | — | 0 |
| (A) | 0.05 | 0 |
| (B) | 0.05 | 0 |
| (71) | 0.05 | 50 |
| (62) | 0.05 | 95 |
| (73) | 0.05 | 60 |
| (55) | 0.05 | 95 |
| (67) | 0.05 | 95 |
| (60) | 0.05 | 100 |
| (54) | 0.05 | 100 |
| (61) | 0.05 | 80 |
| (70) | 0.05 | 90 |

EXAMPLE G

Inhibition of growth of soya beans

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in % of the additional growth of the control plants was calculated. 100% meant that growth had stopped and 0% denoted a growth corresponding to that of the control plants.

The active compounds, active compound concentrations and results can be seen from the table which follows.

Table G

| Inhibiton of growth of soya beans | | |
| --- | --- | --- |
| Active compound | Active compound concentration in % | Inhibition of growth in % |
| — (control) | — | 0 |
| (D) | 0.05 | 0 |
| (A) | 0.05 | 0 |
| (B) | 0.05 | 0 |
| (72) | 0.05 | 25 |
| (62) | 0.05 | 95 |
| (55) | 0.05 | 100 |
| (67) | 0.05 | 100 |
| (60) | 0.05 | 20 |
| (54) | 0.05 | 100 |
| (61) | 0.05 | 90 |
| (70) | 0.05 | 90 |

EXAMPLE H

Defoliation and desiccation of cotton

Solvent: 30 parts by weight of dimethylformamide.
Emulsifier: 1 part by weight of polyoxyethylene sorbitan monolaurate.

To produce a suitable preparation of active compound, 1 part by weight of active compound was mixed with the stated amounts of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet.

After 1 week, the shedding of leaves and the desiccation of the leaves induced by the preparations were rated. The results were compared with those of the untreated control plants.

The degree of defoliation and of desiccation was determined and was designated on a scale of 0–3, as follows:

0 = no action (like the untreated control)
1 = slight action
2 = moderate action
3 = powerful action The active compounds, active compound concentrations and results can be seen from the table which follows.

Table H

| Defoliation and desiccation of cotton | | |
| --- | --- | --- |
| Active compound | Active compound concentration in % | Defoliation and desiccation |
| — (control) | — | 0 |
| (A) | 0.05 | 0 |
| (B) | 0.05 | 0 |
| (62) | 0.05 | 1 |
| (55) | 0.05 | 2 |
| (67) | 0.05 | 2 |
| (54) | 0.05 | 2 |
| (61) | 0.05 | 1 |
| (32) | 0.05 | 3 |
| (70) | 0.05 | 1 |

PREPARATIVE EXAMPLES

Example 1

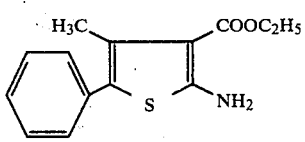 (1)

131 g (1.5 moles) of morpholine were added to a mixture of 201 g (1.5 moles) of methyl benzyl ketone, 204 g (1.8 moles) of cyanoacetic acid ethyl ester and 48 g (1.5 moles) of sulphur in 100 ml of ethanol, while stirring. An exothermic reaction started, during which the temperature was allowed to rise to 60° C. The reaction mixture was left to stand overnight and then poured into water, the oil which separated out was taken up in methylene chloride and the organic phase was washed successively with water and dilute acetic acid. After stripping off the solvent, the residue (387 g), which had partly solidified, was recrystallized from cyclohexane. 166 g of 2-amino-3-ethoxycarbonyl-4-methyl-5-phenyl-thiophene were obtained in this manner in the form of a solid substance of melting point 93° C.

The compounds of the formulae listed in the table which follows were prepared in an analogous manner.

Table 1

$$\underset{R^2}{\overset{R^1}{\diagdown}}\underset{X}{\diagup}\underset{NH-R^3}{\overset{R^4}{\diagdown}}$$

| Example No. | X | $R^1$ | $R^2$ | $R^3$ | $R^4$ | Melting point [°C.] |
|---|---|---|---|---|---|---|
| 2 | S | $CH_3$ | $CH_3$ | H | $-COO-C_2H_5$ | 92 |
| 3 | S | $i-C_4H_9$ | H | H | $-COOC_2H_5$ | 65 |
| 4 | S | —⟨phenyl⟩ | H | H | $-COOC_2H_5$ | 96 |

EXAMPLE 5

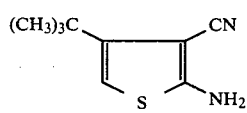 (5)

870 ml (10 moles) of morpholine were added dropwise to a mixture of 1,480 g (10 moles) of 1-tert.-butyl-2,2-dicyanoethylene and 320 g (10 moles) of sulphur in 4 liters of ethanol, while stirring intensively. A temperature of 45°–50° C. was maintained during this addition by initially warming the mixture slightly and later cooling it. After the exothermic reaction had subsided, the mixture was stirred at 50° C. for a further 2 hours, 3 liters of ethanol were then stripped off under reduced pressure and the residue was stirred with 5 liters of ice-water. The product which thereby precipitated was filtered off, washed and dried. 1,750 g of 2-amino-3-cyano-4-tert.-butyl-thiophene of melting point 92° C. were obtained in this manner.

The 1-tert.-butyl-2,2-dicyano-ethylene used as the starting material was prepared as follows:

A mixture of 990 g (15 moles) of malonic acid dinitrile, 2,625 g (26.25 moles) of methyl tert.-butyl ketone, 145 g (1.88 moles) of ammonium acetate, 225 g (3.75 moles) of acetic acid and 2 liters of toluene was boiled, using a water separator, until the amount of water which had been separated off no longer increased (10–13 hours). The dark brown reaction solution was diluted with 2 liters of toluene and then stirred with 5 liters of water, the phases were separated, the organic phase was filtered and the filtrate was evaporated. The residue which remained was subjected to fractional distillation under reduced pressure. 1,616 g of 1-tert.-butyl-2,2-dicyano-ethylene, which had a boiling point of 70° C. under 0.2 mm Hg, were obtained. $n_D^{20}=1.4798$.

According to the gas chromatogram, the degree of purity of the product was 99%.

The compounds given in Examples 6 and 7 were prepared by methods analogous to that described in Example 5.

EXAMPLE 6

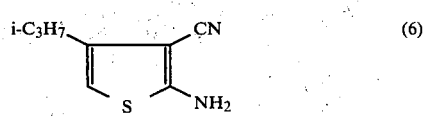 (6)

melting point 70° C.
Starting material:

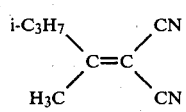

boiling point: 65° C. under 0.15 mm Hg.
$n_D^{20}=1.4706$.

EXAMPLE 7

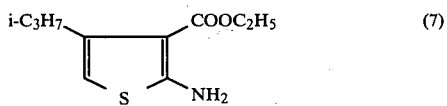 (7)

melting point 62° C.
starting material:

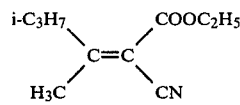

boiling point: 69° C. under 0.2 mm Hg
$n_D^{20}=1.4689$.

EXAMPLE 8

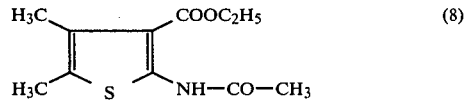 (8)

59.7 g (0.2 mole) of 2-amino-3-ethoxycarbonyl-4,5-dimethyl-thiophene were dissolved in 72 ml of acetic acid, and 33.7 g (0.33 mole) of acetic anhydride were added. After the exothermic reaction had subsided, the reaction mixture was poured into 400 ml of ice-water and the product which precipitated was filtered off and washed with water. 69.7 g of 2-acetylamino-3-ethoxycarbonyl-4,5-dimethylthiophene of melting point 98° C. (after recrystallization from cyclohexane) were obtained in this manner.

The compounds listed in the following table were prepared by methods analogous to that described in Example 8.

Table 2

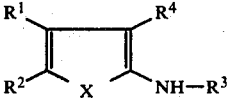

| Example No. | X | $R^1$ | $R^2$ | $R^3$ | $R^4$ | Melting point [°C.] |
|---|---|---|---|---|---|---|
| 9 | S | $CH_3$ | $CH_3$ | $CO-C_2H_5$ | $CO_2-C_2H_5$ | 73 |
| 10 | S | $CH_3$ | $CH_3$ | $CO-i-C_3H_7$ | $CO_2-C_2H_5$ | 46 |
| 11 | S | $CH_3$ | $CH_3$ | $CO-t-C_4H_9$ | $CO_2-C_2H_5$ | 81 |
| 12 | S | $i-C_4H_9$ | H | $CO-CH_3$ | $CO_2-C_2H_5$ | 62 |
| 13 | S | $i-C_4H_9$ | H | $CO-C_2H_5$ | $CO_2-C_2H_5$ | 39 |
| 14 | S | $i-C_4H_9$ | H | $CO-i-C_3H_7$ | $CO_2-C_2H_5$ | 34 |
| 15 | S | $i-C_4H_9$ | H | $CO-t-C_4H_9$ | $CO_2-C_2H_5$ | 67 |
| 16 | S | $C_6H_5$ | H | $CO-CH_3$ | $CO_2-C_2H_5$ | 93 |
| 17 | S | $C_6H_5$ | H | $CO-C_2H_5$ | $CO_2-C_2H_5$ | 68 |
| 18 | S | $C_6H_5$ | H | $CO-i-C_3H_7$ | $CO_2-C_2H_5$ | 92 |
| 19 | S | $C_6H_5$ | H | $CO-t-C_4H_9$ | $CO_2-C_2H_5$ | 112 |
| 20 | S | $i-C_3H_7$ | H | $CO-CH_3$ | CN | 140 |
| 21 | S | $i-C_3H_7$ | H | $CO-C_2H_5$ | CN | 137 |
| 22 | S | $i-C_3H_7$ | H | $CO-CF_3$ | CN | 155 |
| 23 | S | $t-C_4H_9$ | H | $CO-CH_3$ | CN | 160 |
| 24 | S | $t-C_4H_9$ | H | $CO-CF_3$ | CN | 156 |
| 25 | S | $t-C_4H_9$ | H | $CO-C_2H_5$ | CN | 157 |
| 26 | S | $t-C_4H_9$ | H | $CO-i-C_3H_7$ | CN | 136 |

EXAMPLE 27

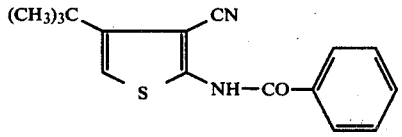 (27)

After adding 29.4 g (0.21 mole) of benzoyl chloride, a mixture of 36 g (0.2 mole) of 2-amino-3-cyano-4-tert.-butyl-thiophene and 200 ml of toluene was boiled until the evolution of hydrogen chloride had ended (4 hours). Thereafter, the reaction mixture was filtered and the filtrate was concentrated on a rotary evaporator. The residue was recrystallized from methanol. 46.4 g of 2-benzoylamino-3-cyano-4-tert.-butyl-thiophene of melting point 130° C. were obtained in this manner.

The compounds listed in the table which follows were prepared by methods analogous to that described in Example 27.

Table 3

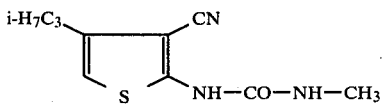

| Example No. | X | $R^1$ | $R^2$ | $R^3$ | $R^4$ | Melting point [°C.] |
|---|---|---|---|---|---|---|
| 28 | S | $t-C_4H_9$ | H | $CO-CH_2Cl$ | CN | 126 |
| 29 | S | $t-C_4H_9$ | H | $CO-t-C_4H_9$ | CN | 173 |
| 30 | S | $t-C_4H_9$ | H | $CO-O-CH_3$ | CN | 114 |
| 31 | S | $t-C_4H_9$ | H | $CO-O-C_6H_5$ | CN | 125 |

EXAMPLE 32

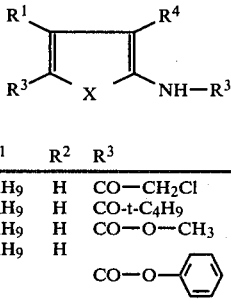 (32)

11.8 ml (0.2 mole) of methyl isocyanate were added to a solution of 33.2 g (0.2 mole) of 2-amino-3-cyano-4-isopropyl-thiophene in 200 ml of toluene. After the exothermic reaction had subsided, the product which precipitated in the solid form was filtered off. Further portions of reaction product were obtained by concentrating the mother liquor. 25 g of 1-(3-cyano-4-isopropyl-thien-2-yl)-3-methyl-urea of melting point 179°–181° C. were obtained in this manner.

The compounds listed in the table which follows were prepared by methods analogous to that described in Example 32.

Table 4

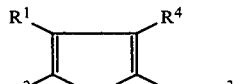

| Example No. | X | $R^1$ | $R^2$ | $R^3$ | $R^4$ | Melting point [°C.] |
|---|---|---|---|---|---|---|
| 33 | S | $t-C_4H_9$ | H | $CO-NH-CH_3$ | CN | 220 |
| 34 | S | $t-C_4H_9$ | H | $CO-NH-CH_2-CH=CH_2$ | CN | 150 |
| 35 | S | $t-C_4H_9$ | H | $CO-NH-n.-C_4H_9$ | CN | 157 |
| 36 | S | $t-C_4H_9$ | H | $CO-NH-C_6H_5$ | CN | 202 |
| 37 | S | $t-C_4H_9$ | H | $CO-NH-C_6H_4Cl$ | CN | 240 |

Table 4-continued

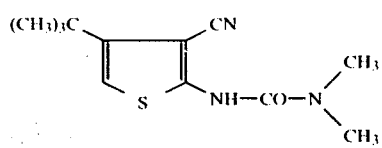

| Example No. | X | R¹ | R² | R³ | R⁴ | Melting point [°C] |
|---|---|---|---|---|---|---|
| 38 | S | t-C₄H₉ | H | ![](Cl-phenyl-CO-NH- with Cl) | CN | 238 |
| 39 | S | t-C₄H₉ | H | ![](Cl-phenyl-CO-NH- with Cl) | CN | 271 |

EXAMPLE 40

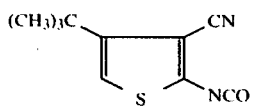
(40)

20.6 g (0.1 mole) of 3-cyano-4-tert.-butyl-thien-2-yl isocyanate were added dropwise to a solution of 6.5 g (0.145 mole) of dimethylamine in 200 ml of toluene at room temperature. After the exothermic reaction had subsided, the mixture was concentrated and the residue was recrystallized from a little toluene. 20.1 g of 1-(3-cyano-4-tert.-butyl-thien-2-yl)-3,3-dimethyl-urea of melting point 140° C. were obtained in this manner.

Preparation of the starting material:

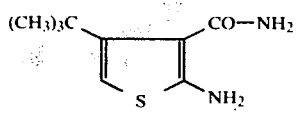

A solution of 90 g (0.5 mole) of 2-amino-3-cyano-4-tert.-butyl-thiophene in 300 ml of chlorobenzene was added dropwise to a solution of 150 g of phosgene in 1.5 liters of chlorobenzene at 0°–5° C. Thereafter, the mixture was slowly heated to the boil, while passing further phosgene in, and excess phosgene was then driven off by passing dry nitrogen in. For working up, the solvent was stripped off under reduced pressure and the residue was distilled. 62 g of 3-cyano-4-tert.-butyl-thien-2-yl isocyanate, which boiled at 163° C. under a pressure of 20 mm Hg, were obtained in this manner.
Melting point: 61°–64° C.

EXAMPLE 41

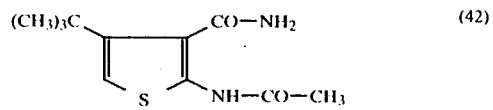
(41)

A mixture of 180 g (1 mole) of 2-amino-3-cyano-4-tert.-butyl-thiophene and 750 ml of 95–97% strength sulphuric acid was stirred at 100°–110° C. for one hour, whereupon a slightly exothermic reaction started, so that when a temperature of 100° C. was reached no further heating was required. The reaction mixture was left to cool and was stirred into 5 liters of ice-water and neutralized with about 3 liters of 25% strength aqueous ammonia solution. The solid product which precipitated was filtered off, washed with water and dried at 50° C. 194 g of 2-amino-3-aminocarbonyl-4-tert.-butyl-thiophene of melting point 145° C. were obtained in this manner.

EXAMPLE 42

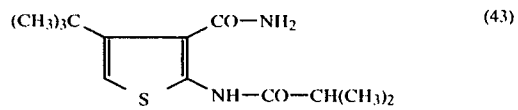
(42)

21.2 g (0.21 mole) of triethylamine were first added to a suspension of 39.6 g (0.2 mole) of 2-amino-3-aminocarbonyl-4-tert.-butyl-thiophene in 300 ml of toluene, and 16.5 g (0.21 mole) of acetyl chloride were then added dropwise. After the exothermic reaction had ended, the mixture was worked up by filtering off the solid product and washing it with water. 38.6 g of 2-acetylamino-3-aminocarbonyl-4-tert.-butyl-thiophene of melting point 251° C. were obtained in this manner.

EXAMPLE 43

(CH₃)₃C—[thiophene]—CO—NH₂, NH—CO—CH(CH₃)₂ (43)

22.2 g (0.21 mole) of isobutyryl chloride were added dropwise to a solution of 39.6 g (0.2 mol) of 2-amino-3-aminocarbonyl-4-tert.-butylthiophene in 200 ml of pyridine, while cooling, at a temperature between 10° C. and 30° C. After 30 minutes, the reaction mixture was poured into 2 liters of ice-water and the solid product which precipitated was filtered off, washed with water and dried at 50° C. 42 g of 2-isobutyrylamino-3-aminocarbonyl-4-tert.-butylthiophene, which, after recrystallization from a dimethylformamide/methanol mixture had a melting point of 226° C., were obtained in this manner.

The compound indicated in the example which follows was prepared by a method analogous to that described in Example 43.

EXAMPLE 44

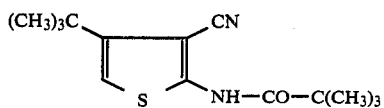 (44)

melting point: 221° C.

EXAMPLE 45

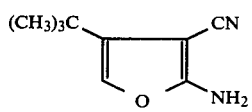 (45)

174 g (2 moles) of morpholine were added dropwise to a solution of 232 g (2 moles) of hydroxy-pinacolone and 132 g (2 moles) of malonic acid dinitrile in 500 ml of dimethylformamide, while cooling, in a manner such that the internal temperature did not rise above 40° C. After the reaction had ended, the reaction mixture was stirred into 5 liters of ice-water. The solid product which thereby precipitated was filtered off, washed with water and dried. 170 g of 2-amino-3-cyano-4-tert.-butyl-furan of melting point 86° C. were obtained in this manner.

The compounds indicated in the examples which follow were prepared by methods analogous to that described in Example 45.

EXAMPLE 46

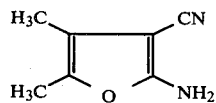 (46)

melting point: 167° C.

EXAMPLE 47

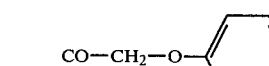 (47)

melting point: 87° C.

EXAMPLE 48

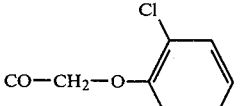 (48)

melting point 202° C.

EXAMPLE 49

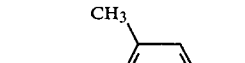 (49)

20.4 g (0.1 mole) of 2-amino-3-cyano-4,5-dimethylfurane and 17.5 g (0.155 mole) of chloroacetyl chloride were boiled in 200 ml of toluene until the evolution of hydrogen chloride had subsided. Thereafter, the solvent was evaporated off under reduced pressure and the residue was recrystallized from ethyl acetate. 26 g of 2-chloroacetylamino-3-cyano-4,5-dimethylfurane of melting point 114° C. were obtained in this manner.

The compounds listed in the table which follows were prepared by methods analogous to that described in Example 49.

Table 5

| Example No. | X | $R^1$ | $R^2$ | $R^3$ | $R^4$ | Melting point [°C.] |
|---|---|---|---|---|---|---|
| 50 | O | $CH_3$ | $CH_3$ | $CO-C_2H_5$ | CN | 97 |
| 51 | O | $CH_3$ | $CH_3$ | $CO$-$i$-$C_3H_7$ | CN | 150 |
| 52 | O | $CH_3$ | $CH_3$ | $CO-CH_2-O-$C₆H₅ | CN | 126 |
| 53 | O | $CH_3$ | $CH_3$ | $CO-CH_2-O-$(2-Cl-C₆H₄) | CN | 136 |
| 54 | O | $CH_3$ | $CH_3$ | $CO-CH_2-O-$(3-CH₃-4-Cl-C₆H₃) | CN | 156 |

Table 5-continued $$\begin{array}{c} R^1 \quad R^4 \\ \diagdown \diagup \\ X \\ \diagup \diagdown \\ R^2 \quad NH-R^3 \end{array}$$

| Example No. | X | R¹ | R² | R³ | R⁴ | Melting point [°C.] |
|---|---|---|---|---|---|---|
| 55 | O | CH₃ | CH₃ | CO—CH₂—O—(2,4,5-trichlorophenyl) | CN | 179 |
| 56 | O | t-C₄H₉ | H | CO—CH₂—Cl | CN | 83 |
| 57 | O | t-C₄H₉ | H | CO-i-C₃H₇ | CN | 117 |
| 58 | O | t-C₄H₉ | H | CO-t-C₄H₉ | CN | 160 |
| 59 | O | t-C₄H₉ | H | CO—phenyl | CN | 139 |
| 60 | O | t-C₄H₉ | H | CO—CH₂—O—phenyl | CN | 128 |
| 61 | O | t-C₄H₉ | H | CO—CH₂—O—(2-methyl-4-chlorophenyl) | CN | 109 |
| 62 | O | t-C₄H₉ | H | CO—CH₂—O—(2,4,5-trichlorophenyl) | CN | 170 |
| 63 | O | phenyl | H | CO—CH₂—Cl | CN | 168 |
| 64 | O | phenyl | H | CO-i-C₃H₇ | CN | 148 |
| 65 | O | phenyl | H | CO-t-C₄H₉ | CN | 148 |
| 66 | O | phenyl | H | CO—CH₂—O—phenyl | CN | 156 |
| 67 | O | phenyl | H | CO—CH₂—O—(2,4,5-trichlorophenyl) | CN | 204 |
| 68 | O | phenyl | phenyl | CO—CH₂—Cl | CN | 192 |
| 69 | O | phenyl | phenyl | CO—CH₂—O—phenyl | CN | 126 |

Table 5-continued

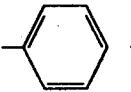

| Example No. | X | R¹ | R² | R³ | R⁴ | Melting point [°C] |
|---|---|---|---|---|---|---|
| 70 | O |  | 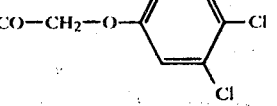 | CO—CH₂—O— (2,4,5-trichlorophenyl) | CN | 214 |

EXAMPLE 71

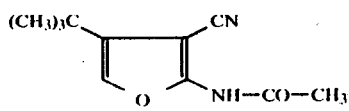 (71)

16.4 g (0.1 mole) of 2-amino-3-cyano-4-tert.-butylfuran were heated to 100° C. with 24 ml (0.4 mole) of acetic acid and 10.4 ml (0.11 mole) of acetic anhydride for one hour. Thereafter, the reaction mixture was evaporated under reduced pressure and the residue was recrystallized from a mixture of toluene/cyclohexane (1:2). 17.2 g of 2-acetylamino-3-cyano-4-tert.-butyl-furan of melting point 135° C. were obtained in this manner.

The compounds indicated in the examples which follow were prepared by methods analogous to that described in Example 71.

EXAMPLE 72

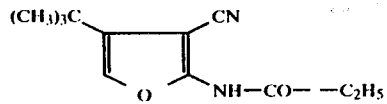 (72)

melting point 103° C.

EXAMPLE 73

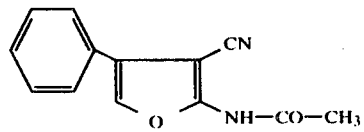 (73)

melting point: 148° C.

EXAMPLE 74

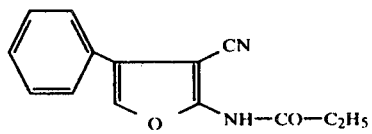 (74)

melting point: 150° C.

EXAMPLE 75

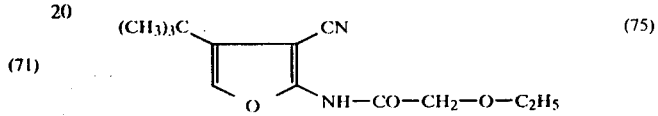 (75)

26.2 g (0.2 mole) of ethoxyacetyl chloride were added dropwise to a solution of 32.8 g (0.2 mole) of 2-amino-3-cyano-4-tert.-butyl-furan in 200 ml of dimethylformamide at room temperature. After the moderately exothermic reaction had subsided (rise in temperature from 23° C. to 38°), the reaction mixture was poured into ice-water. The solid product thereby obtained was filtered off and recrystallized, in the moist state, from a little methanol. 39.3 g of 2-ethoxyacetylamino-3-cyano-4-tert.-butyl-furan of melting point 98° C. were obtained in this manner.

The compounds indicated in the examples which follow were prepared by methods analogous to that described in Example 75.

EXAMPLE 76

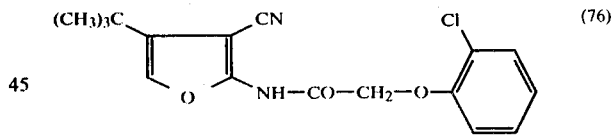 (76)

melting point: 116° C.

EXAMPLE 77

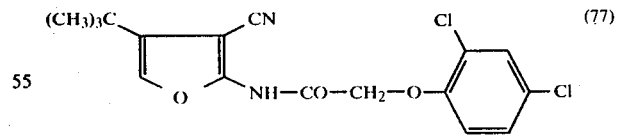 (77)

melting point: 139° C.

EXAMPLE 78

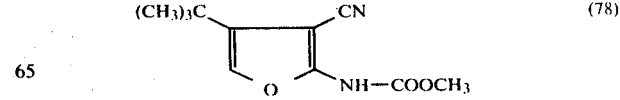 (78)

melting point: 103° C.

EXAMPLE 79

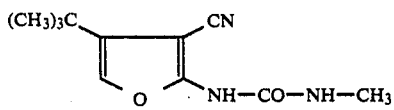

A solution of 7.8 g (0.041 mole) of 3-cyano-4-tert.-butyl-fur-2-yl isocyanate in 30 ml of toluene was added dropwise to a solution of 1.6 g (0.052 mole) of methylamine in 30 ml of toluene. Thereafter, the mixture was worked up by concentrating it under reduced pressure and recrystallizing the residue from toluene. 6.8 g of 1-(3-cyano-4-tert.-butyl-fur-2-yl)-3-methylurea of melting point 163° C. were obtained in this manner.

The 3-cyano-4-tert.-butyl-fur-2-yl isocyanate required as the starting material was prepared by phosgenation of 2-amino-3-cyano-4-tert.-butyl-furan.
Melting point: 39°–41° C.
Boiling point: 71° C. under 0.6 mm Hg.

The compounds indicated in the examples which follow were prepared by methods analogous to that described in Example 79.

EXAMPLE 80

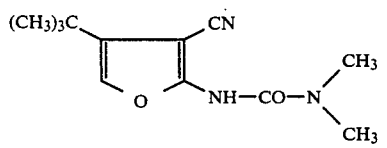

melting point: 155° C.

EXAMPLE 81

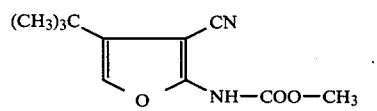

melting point: 103° C.

It will be understood that the specification and examples are illustrative but not limitative of the present invention and that other embodiments within the spirit and scope of the invention will suggest themselves to those skilled in the art.

What is claimed is:

1. Method for regulating the growth of plants which method comprises applying to the plants or their habitat, effective amounts of a heterocyclic compound of the formula

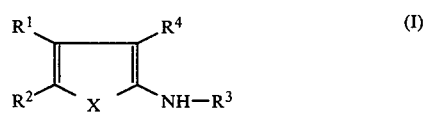

in which
$R^1$ is alkyl of up to 6 carbon atoms, aryl of 6 on 10 carbon atoms or substituted aryl carrying at least one substituent selected from halogen, alkyl of up to 4 carbon atoms, haloalkyl of to 4 carbon atoms, alkoxy of up to 4 carbon atoms, alkylthio of up to 4 carbon atoms, alkylsulfonyl of up 4 carbon atoms and nitro;

$R^2$ is hydrogen, alkyl of up to 6 carbon atoms, aryl of 6 or 10 carbon atoms, or substituted aryl having at least one substituent selected from halogen, alkyl with 1 to 4 carbon atoms, haloalkyl with 1 to 4 carbon atoms and 1 to 5 halogen atoms, alkoxy with 1 to 4 carbon atoms, alkylthio with 1 to 4 carbon atoms and nitro, $R^3$ is hydrogen or the radical

in which
Y is oxygen and
$R^5$ is alkyl with 1 to 6 carbon atoms, haloalkyl with 1 to 4 carbon atoms and 1 to 5 halogen atoms, alkoxyalkyl with 1 to 4 carbon atoms in the alkyl part and 1 to 4 carbon atoms in the alkoxy part, aryloxyalkyl, which has 6 or 10 carbon atoms in the aryloxy part and 1 to 4 carbon atoms in the alkyl part and optionally carrying one or more substituents on the aryloxy part selected from halogen, alkyl with 1 to 4 carbon atoms, haloalkyl with 1 to 4 carbon atoms and 1 to 5 halogen atoms; alkoxy with 1 to 4 carbon atoms; aryl with 6 or 10 carbon atoms, substituted aryl carrying one or more substituents selected from halogen, alkyl with 1 to 4 carbon atoms or haloalkyl with 1 to 4 carbon atoms and 1 to 5 halogen atoms, alkoxy, alkylthio, and alkylsulphonyl with 1 to 4 carbon atoms and nitro; aryloxy with 6 or 10 carbon atoms substituted aryloxy having at least one substituent selected from halogen, alkyl with 1 to 4 carbon atom, haloalkyl with 1 to 4 carbon atoms and 1 to 5 halogen atoms, alkoxy, alkylthio, alkylsulphonyl with 1 to 4 carbon atoms and nitro; monoalkylamino with 1 to 4 carbon atoms; dialkylamino with 1 to 4 carbon atoms in each alkyl group; alkenylamino with up to 4 carbon atoms; dialkenylamino with up to 4 carbon atoms in each alkenyl group; arylamino with 6 or 10 carbon atoms substituted arylamino carrying one or more substituents selected from halogen, alkyl with 1 to 4 carbon atoms, haloalkyl with 1 to 4 carbon atoms and 1 to 5 halogen atoms, alkoxy with 1 to 4 carbon atoms, alkylthio with 1 to 4 carbon atoms, alkylsulphonyl with 1 to 4 carbon atoms and nitro $R^4$ is cyano or the grouping -$COR^8$ in which $R^8$ is alkoxy or amino, and X is oxygen or sulfur.

2. Method as claimed in claim 1 wherein $R^1$ is alkyl of up to 4 carbon atoms.

3. Method as claimed in claim 1 wherein $R^1$ is optionally substituted aryl of 6 or 10 carbon atoms in the aryl moiety.

4. Method as claimed in claim 1 wherein $R^2$ is hydrogen.

5. Method as claimed in claim 1 wherein $R^2$ is alkyl of 1 to 4 carbon atoms.

6. Method as claimed in claim 1 wherein $R^2$ is optionally substituted aryl of from 6 or 10 carbon atoms in the aryl moiety.

7. Method as claimed in claim 1 wherein $R^3$ is hydrogen.

8. Method as claimed in claim 1 wherein $R^3$ is the radical

9. Method as claimed in claim 8 wherein Y is oxygen.

10. Method as claimed in claim 8 wherein $R^5$ is alkyl, haloalkyl or alkoxyalkyl of from 1 to 4 carbon atoms per alkyl moiety.

11. Method as claimed in claim 8 wherein $R^5$ is aryloxyalkyl optionally substituted in the aryloxy moiety and having from 6 or 10 carbon atoms in the aryl moiety and 1 to 4 carbon atoms in the alkyl moiety.

12. Method as claimed in claim 8 wherein $R^5$ is alkoxy of up to 4 carbon atoms.

13. Method as claimed in claim 8 wherein $R^5$ is optionally substituted aryl or aryloxy of from 6 or 10 carbon atoms in the aryl moiety.

14. Method as claimed in claim 8 wherein $R^5$ is monoalkylamino, dialkylamino, alkenylamino, or dialkenylamino with up to 4 carbon atoms per alkyl or alkenyl moiety.

15. Method as claimed in claim 8 wherein $R^5$ is optionally substituted arylamino of from 6 or 10 carbon atoms in the aryl moiety.

16. Method as claimed in claim 1 wherein $R^4$ is cyano.

17. Method as claimed in claim 1 wherein $R^4$ is the radical $-COR^8$.

18. Method as claimed in claim 17 wherein $R^8$ alkoxy of up to 4 carbon atoms.

19. Method as claimed in claim 17 wherein $R^8$ is amino.

20. Method as claimed in claim 1 wherein X is oxygen.

21. Method as claimed in claim 1 wherein X is sulfur.

22. Method as claimed in claim 1 wherein said compound is 2-amino-3-ethoxycarbonyl-4-methyl-5-phenyl-thiophene.

23. Method as claimed in claim 1 wherein said compound is 2-amino-ethoxycarbonyl-4,5-dimethyl-thiophene.

24. Method as claimed in claim 1 wherein said compound is 2-benzoylamino-3-cyano-4-tert.butyl-thiophene.

25. Method as claimed in claim 1 wherein said compound is 2-(2,4,5-trichlorophenoxymethylcarbonyl)-amino-3-cyano-4-tert.butyl-furane.

26. Method as claimed in claim 1 wherein said compound is 2-(2,4,5-trichlorophenoxymethylcarbonyl)-amino-3-cyano-4,5-diphenyl-furane.

27. Method as claimed in claim 1 wherein said compound is 2-propionylamino-3-cyano-4-tert.-butyl-furane.

28. Method as claimed in claim 1 wherein said compound is selected from 2-amino-3-ethoxycarbonyl-4-methyl-5-phenyl-thiophene, 3-ethoxycarbonyl-4,5-dimethylthiophene, 2-benzoylamino-3-cyano-4-tert.-butyl-thiophene, 2-(2,4,5-trichlorophenoxymethylcarbonyl)-amino-3-cyano-4-tert.-butyl-furane, 2-(2,4,5-trichlorophenoxymethylcarbonyl)-amino-3-cyano-4,5-diphenyl-furane and 2-propionylamino-3-cyano-4-tert.-butyl-furane.

* * * * *